(12) United States Patent
Bergman

(10) Patent No.: US 7,956,607 B2
(45) Date of Patent: Jun. 7, 2011

(54) DIGITAL FERROMAGNETIC PART INSPECTION

(75) Inventor: Robert William Bergman, Scotia, NY (US)

(73) Assignee: General Electric Company, Schenectady, NY (US)

( * ) Notice: Subject to any disclaimer, the term of this patent is extended or adjusted under 35 U.S.C. 154(b) by 473 days.

(21) Appl. No.: 12/206,851

(22) Filed: Sep. 9, 2008

(65) Prior Publication Data

US 2010/0060274 A1 Mar. 11, 2010

(51) Int. Cl.
*G01N 27/72* (2006.01)
(52) U.S. Cl. ........................................ 324/228; 324/240
(58) Field of Classification Search ................. 324/228, 324/234, 238–240
See application file for complete search history.

(56) References Cited

U.S. PATENT DOCUMENTS

| | | | |
|---|---|---|---|
| 5,315,234 A | 5/1994 | Sutton, Jr. et al. | |
| 5,371,462 A | 12/1994 | Hedengren et al. | |
| 5,389,876 A | 2/1995 | Hedengren et al. | |
| 5,442,286 A | 8/1995 | Sutton, Jr. et al. | |
| 6,184,680 B1 * | 2/2001 | Shinoura et al. | 324/252 |
| 6,812,697 B2 | 11/2004 | McKnight et al. | |
| 2002/0121896 A1 * | 9/2002 | Kato et al. | 324/232 |
| 2008/0309329 A1 * | 12/2008 | Kahlman et al. | 324/228 |
| 2009/0045809 A1 * | 2/2009 | Kasajima et al. | 324/252 |

* cited by examiner

*Primary Examiner* — Bot L LeDynh
(74) *Attorney, Agent, or Firm* — Hoffman Warnick LLC; Ernest G. Cusick

(57) ABSTRACT

Digital ferromagnetic part inspection system and method use a magnetizer for magnetizing a ferromagnetic part to be inspected, wherein a defect in or near a surface of the ferromagnetic part causes an external magnetic field. A magnetic field sensing element is positioned near the ferromagnetic part for sensing the external magnetic field. An inspection module identifies the defect in or near the surface of the ferromagnetic part by interpreting data collected by the magnetic field sensing element in response to the magnetic field sensing element being placed near the ferromagnetic part.

8 Claims, 6 Drawing Sheets

US 7,956,607 B2

DIGITAL FERROMAGNETIC PART INSPECTION

BACKGROUND OF THE INVENTION

Embodiments of the invention relate generally to defect inspection in ferromagnetic parts. More particularly, embodiments of the invention relate to ferromagnetic part inspection using digital magnetic testing.

Inspection of parts to ensure proper fabrication is a necessary step in practically any manufacturing process. Typically, radiography and/or ultrasound are used to inspect the inside of parts, and magnetic particle testing is used to inspect for defects in or near a surface of a part. Magnetic particle testing identifies cracks near a surface of a ferromagnetic part by exposing the part to a magnetic field and flowing small magnetic particles such as soft iron particles across the part, either by air or another fluid. Any defect such as a crack in the part causes the magnetic flux to leave the part, creating two new magnetic poles that attract the small magnetic particles. Hence, accumulation of the magnetic particles in an area on the part indicates a potential defect in the area.

BRIEF DESCRIPTION OF THE INVENTION

A first aspect of the disclosure provides a system comprising: a magnetizer for magnetizing a ferromagnetic part to be inspected, wherein a defect in or near a surface of the ferromagnetic part causes an external magnetic field; a magnetic field sensing element for positioning near the ferromagnetic part for sensing the external magnetic field; and an inspection module for identifying the defect in or near the surface of the ferromagnetic part by interpreting data collected by the magnetic field sensing element in response to the magnetic field sensing element being placed near the ferromagnetic part.

A second aspect of the disclosure provides a method comprising: magnetizing a ferromagnetic part to be inspected, wherein a defect in or near a surface of the ferromagnetic part causes an external magnetic field; positioning a magnetic field sensing element near the ferromagnetic part for sensing the external magnetic field; identifying the defect in or near the surface of the ferromagnetic part by interpreting data collected by the magnetic field sensing element in response to the magnetic field sensing element being placed near the ferromagnetic part; and creating a data storage file regarding any identified defect in or near the surface of the ferromagnetic part.

These and other aspects, advantages and salient features of the invention will become apparent from the following detailed description, which, when taken in conjunction with the annexed drawings, where like parts are designated by like reference characters throughout the drawings, disclose embodiments of the invention.

DETAILED DESCRIPTION OF THE INVENTION

Figure 1:
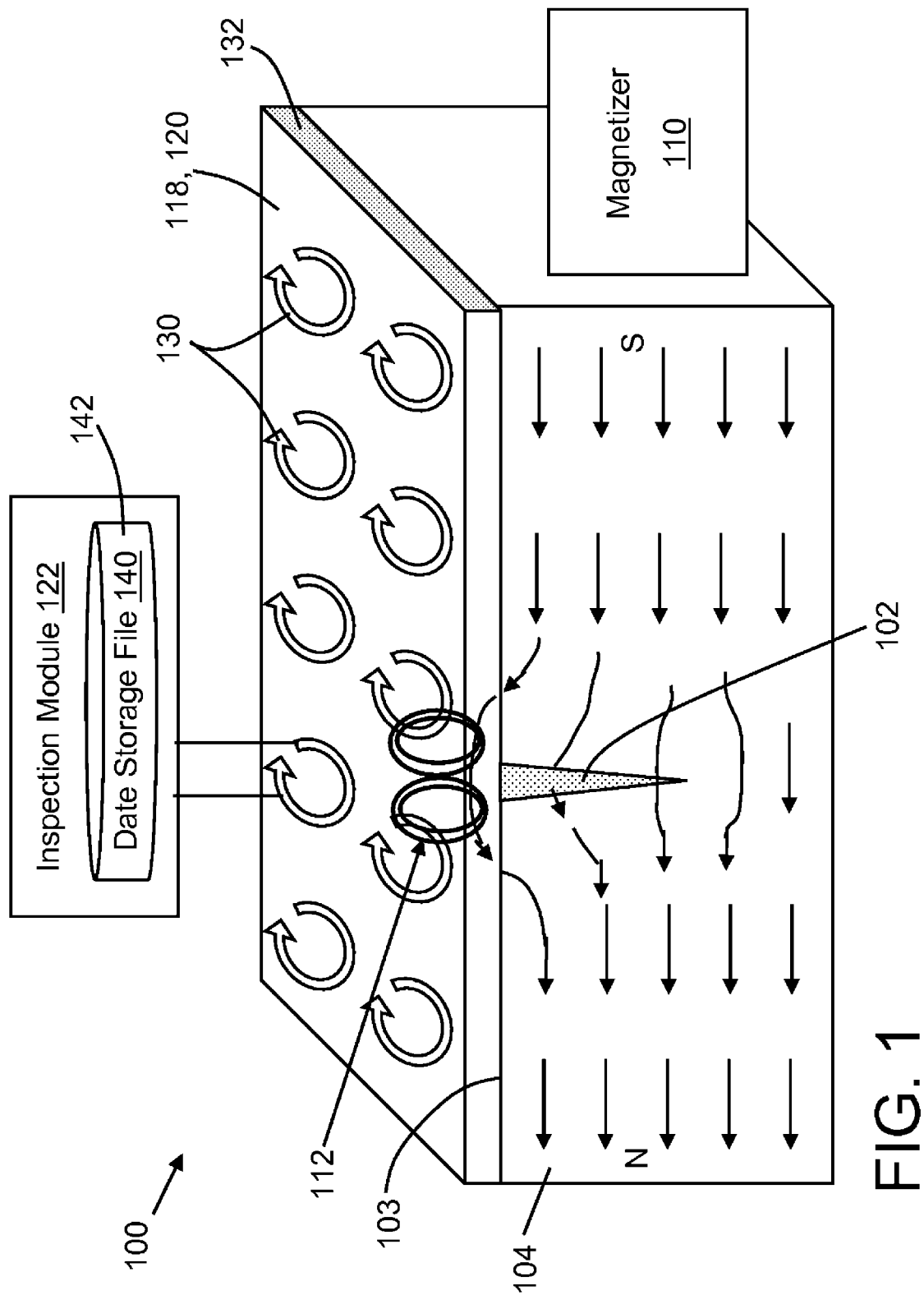
FIG. 1 shows a perspective schematic diagram of a digital ferromagnetic part inspection system.
Figure 4:
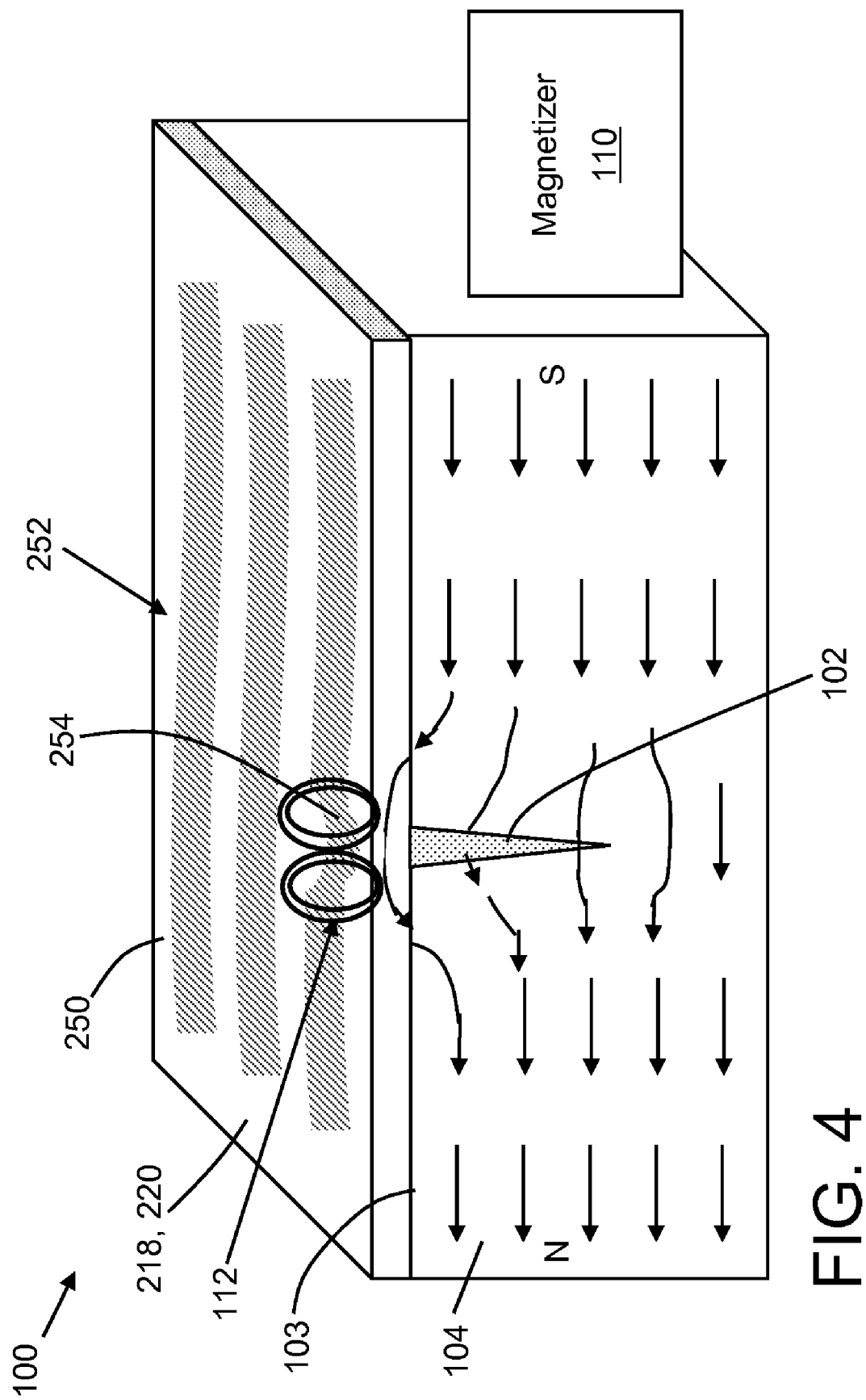
FIG. 4 shows a perspective view of the magnetic field sensing element of FIG. 3 applied to a defective ferromagnetic part.

Referring to the drawings, various embodiments of a digital ferromagnetic part inspection system 100, 200 are illustrated. As shown in FIGS. 1 and 4, for example, system 100, 200 detects a defect 102 in or near a surface 103 of a ferromagnetic part 104. System 100, 200 includes a magnetizer 110 for magnetizing ferromagnetic part 104 to be inspected. Magnetizer 110 may include any now known or later developed systems for creating a magnetic field through part 104 such as those used for conventional magnetic particle inspection. As understood, when magnetized, a defect 102 in ferromagnetic part 104 causes an external magnetic field 112 to be generated from the part.

In contrast to conventional ferromagnetic part testing, system 100, 200 also includes a magnetic field sensing element 118 for positioning near the ferromagnetic part for sensing external magnetic field 112, i.e., for detecting defect 102, and an inspection module 122 for identifying defect 102 in part 104 by interpreting data collected by magnetic field sensing element 118 in response to the sheet being placed near the part. In one embodiment, magnetic field sensing element 118 includes a sheet 120; however, other structures may be used within the scope of the invention.

Figure 2:
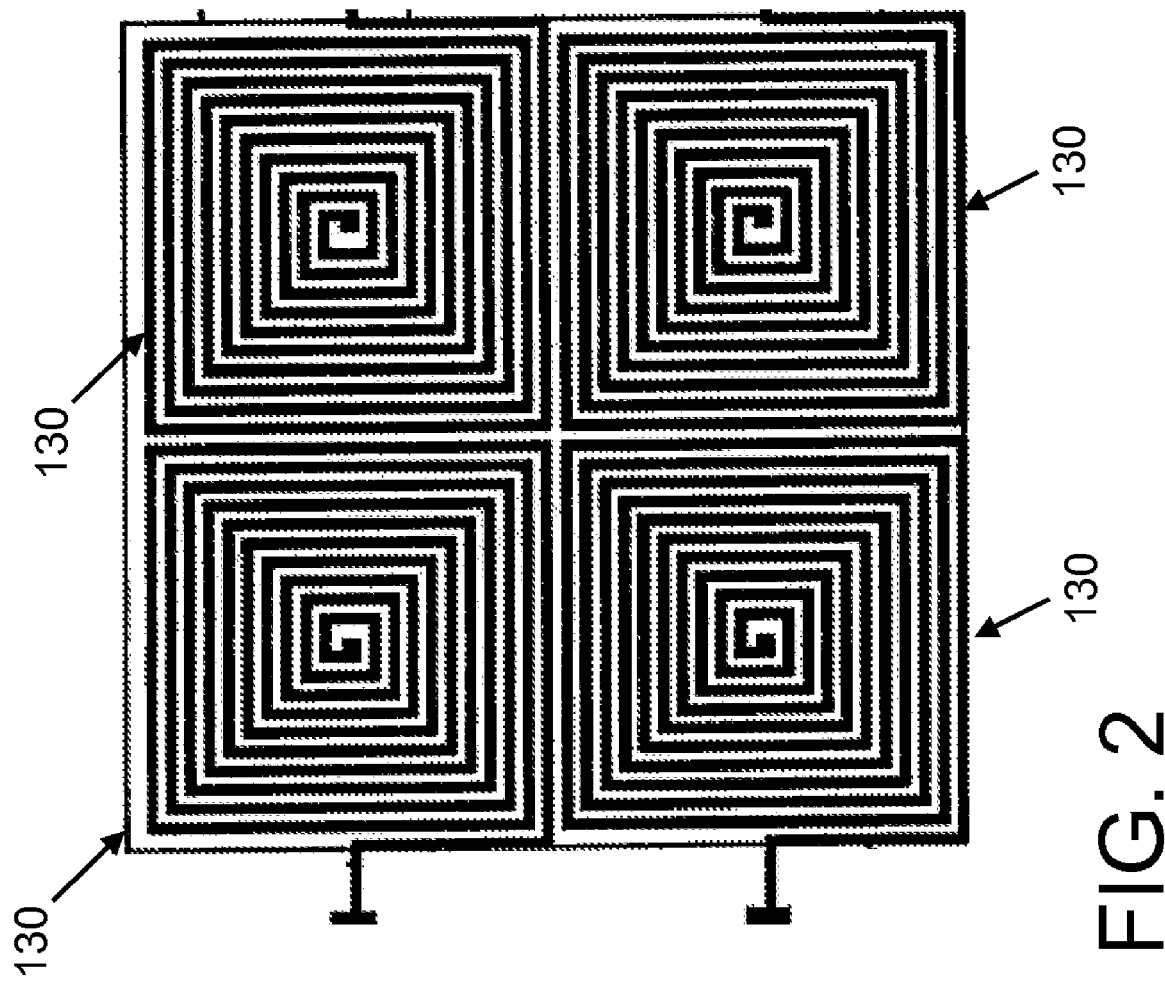
FIG. 2 shows a plan view of an illustrative set of coils used in one embodiment of the system of FIG. 1.

Sheet 120 and inspection module 122 may take a variety of forms. In one embodiment, shown in FIGS. 1-2 relative to system 100, sheet 120 includes an array of current sensing coils 130 in a sheet of material 132. Each coil 130 (only one shown for clarity) is operatively coupled to inspection module 122. FIG. 2 shows an illustrative set of coils 130, which may include a metal such as copper or aluminum encased in material sheet 132, which may include a plastic or other non-conducting material. Sheet 120 provides structure similar to conventional Eddy current inspection coil arrays. However, Eddy current inspection is based on the principle of electromagnetic induction in which a drive coil is employed to induce eddy currents within the material under inspection, and secondary magnetic fields resulting from the eddy currents are detected by a sense coil, generating signals which are subsequently processed for the purpose of detecting flaws. The probe must be moved to sense and cannot be used on a ferromagnetic part. In contrast, for system 100, sensing sheet 120 detects external magnetic field 112 created by magnetizer 110 via defect 102, i.e., no magnetic field is created by coils 130.

In operation, inspection module 122 collects data in the form of electrical response information from the array of current sensing coils 130 caused by external magnetic field 112. Where inspection module 122 detects a change in current in a current sensing coil(s) 130, a defect is identified. In this embodiment, inspection module 122 may include any microprocessor-based analyzer capable of detecting a change in current over the array of current sensing coils 130. In this manner, inspection module 122 may interpret the data in real-time with magnetizer 110 magnetizing part 104. In addition, based on this information, inspection module 122 can create a computer readable medium 140 (or data storage file) including data regarding an identified defect 102 in or near surface 102 of ferromagnetic part 104. Computer readable medium 140 may include, for example, a digital image of defects in part 104. A storage unit 142 may be provided for storing a result (e.g., an image or other data storage file) from the inspection module.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer usable program code may be transmitted using any appropriate medium, including but not limited to wireless, wireline, optical fiber cable, RF, etc.

Figure 3:
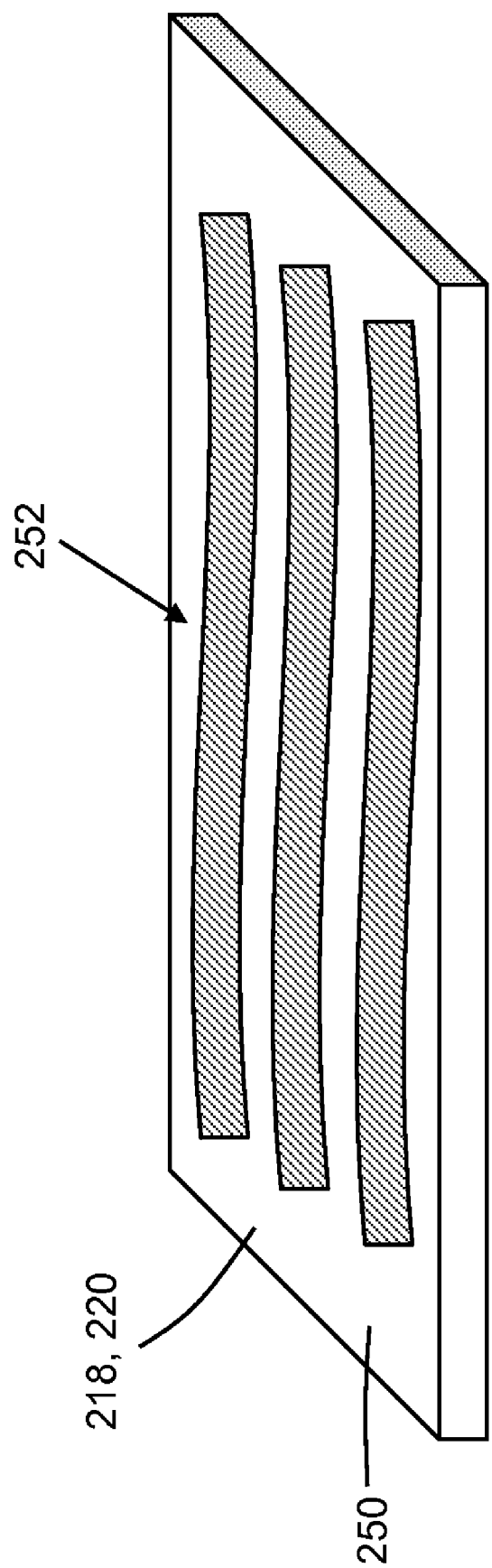
FIG. 3 shows perspective view of a magnetic field sensing element used in another embodiment of the system.
Figure 5:
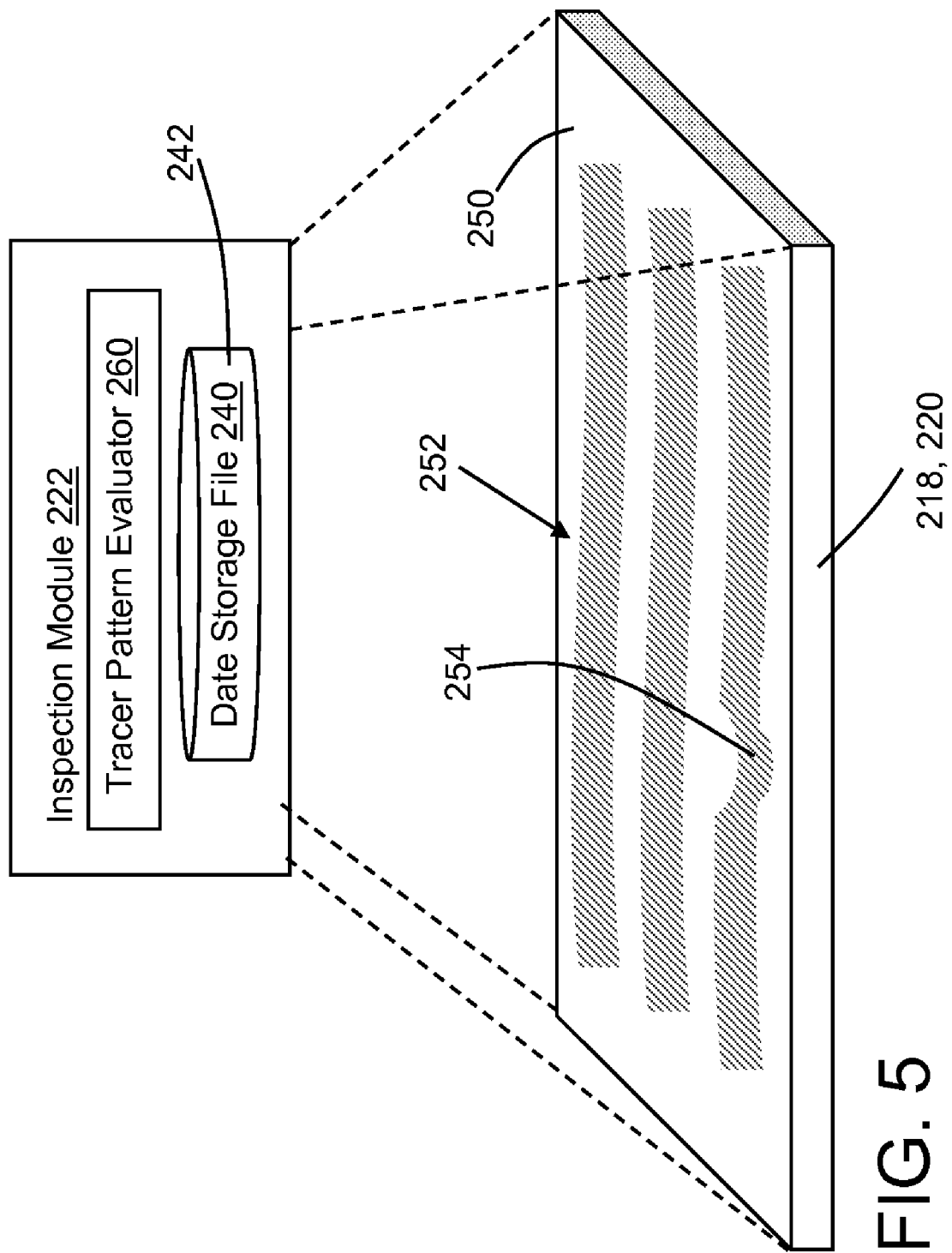
FIG. 5 shows the magnetic field sensing element of FIG. 4 being inspected by an inspection module according to another embodiment of the invention.

In another embodiment, shown in FIGS. 3-5, system 200 includes a magnetic field sensing element 218 in the form of a sheet 220 that includes a magnetic sheet material 250 including a pre-determined tracer pattern 252, e.g., a pattern similar to data stored on a magnetic storage tape or disc. When magnetic sheet material 250 is placed near part 104 under magnetization by magnetizer 110, as shown in FIG. 4, external magnetic field 112 causes a change 254 in tracer pattern 252. As shown in FIG. 5, an inspection module 222 evaluates data that includes change 254 in pre-determined tracer pattern 252 caused by the external magnetic field 112, which identifies defect 102 in or near surface 103 of part 104. Inspection module 222 may include any microprocessor-based system including a tracer pattern evaluator 260 for determining change 254 in pre-determined tracer pattern 252. Tracer pattern evaluator 260 may include, for example, a reader for reading the tracer pattern after exposure to the part and comparing the tracer pattern read from magnetic sheet material 250 to an original tracer pattern (FIG. 3) by use of, for example, a differential amplifier. The output of the differential amplifier would be the difference between the two signals and thus the pattern of defect 102. Based on this information, inspection module 222 can create a computer readable medium 240 including data regarding an identified defect 102 in or near surface 103 of ferromagnetic part 104. Computer readable medium 240 may include, for example, a digital image of defects in part 104. A storage unit 242 may be provided for storing a result (e.g., an image or other data storage file) from the inspection module.

In either of the above-described embodiments, the data collected and evaluated by inspection module 122, 222 allows for determination of a location and size of defect 102 in ferromagnetic part 104. Inspection module 122, 222 may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, inspection module 122, 222 may take the form of a computer program product embodied in any tangible medium of expression having computer-usable program code embodied in the medium.

System 100, 200 via magnetic field sensing elements 118, 218 (sheets 120, 220) can be applied to practically any surface 103 of part 104. Hence, system 100, 200 remove the need for messy magnetic particles that cannot be applied in clean areas, material exclusion zones or inaccessible areas (e.g., small areas or vertical surfaces) of a part. In addition, system 100, 200 also provide a clean mechanism for obtaining a permanent record (data storage file 140, 240 in a computer readable medium) proving that part 104 passed inspection.

Figure 6:
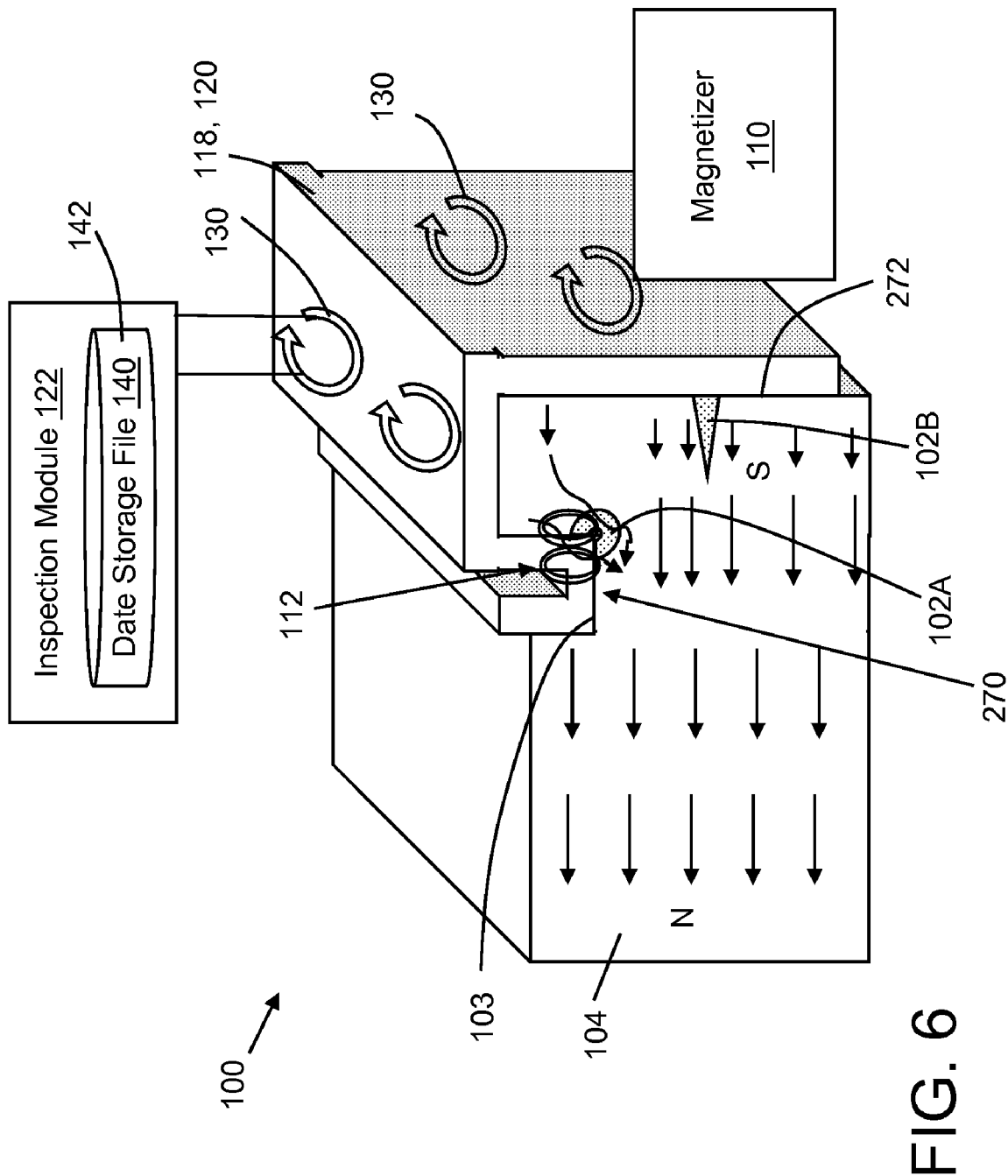
FIG. 6 shows a system according to embodiments of the invention applied to a small opening and vertical surface of a ferromagnetic part.

Although particular mechanisms have been disclosed herein for sensing external magnetic field 112 caused by a defect 102, other means may also be possible and are considered within the scope of the invention. In addition, the term "sheet" has been used to describe the elements used to sense the external magnetic field. It is understood, however, that the sheet could be any element that can be flat or shaped to go around corners, and is thin relative to its length and width. Further, there is no limit on the length and width of the sheet as it may be sized to fit into practically any small opening. For example, FIG. 6 shows application of a sheet 120 in a small area or opening 270 and/or on a substantially vertical surface 272 of a ferromagnetic part 104. Other possible magnetic field sensing elements may include a group of coils such as described herein within a structure that is not in a sheet form. For example, magnetic field sensing element 118, 218 may include any structure capable of sensing external magnetic field 112, and may be flexible such that it may be formed about corners of part 104. Although not shown, it is understood that magnetizer 110 may be moved to change the direction of the magnetic field to create different external magnetic fields 112 to allow for detection of defects (e.g., defects 102A, 102B) in different areas of part 104. Although system 100 is shown used in FIG. 6, system 200 (FIGS. 3-5) may be equally applicable.

The terms "first," "second," and the like, herein do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context, (e.g., includes the degree of error associated with measurement of the particular quantity). The suffix "(s)" as used herein is intended to include both the singular and the plural of the term that it modifies, thereby including one or more of that term (e.g., the metal(s) includes one or more metals).

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A system comprising:
a magnetizer for magnetizing a ferromagnetic part to be inspected, wherein a defect in or near a surface of the ferromagnetic part causes an external magnetic field;
a magnetic field sensing element for positioning near the ferromagnetic part for sensing the external magnetic field, wherein the magnetic field sensing element includes a magnetic sheet material including a pre-determined tracer pattern; and
an inspection module for identifying the defect in or near the surface of the ferromagnetic part by interpreting data collected by the magnetic field sensing element in response to the magnetic field sensing element being placed near the ferromagnetic part, wherein the data includes a physical change in the pre-determined tracer pattern caused by the external magnetic field.

2. The system of claim 1, wherein the magnetic field sensing element includes a magnetic field sensing sheet.

3. The system of claim 2, wherein the inspection module includes a tracer pattern evaluator for determining the change in the pre-determined tracer pattern.

4. The system of claim 1, wherein the magnetic field sensing element is flexible.

5. The system of claim 1, further comprising a storage unit for storing a result from the inspection module.

6. The system of claim 1, wherein the inspection module determines a location and size of the defect in or near the surface of the ferromagnetic part.

7. The system of claim 1, wherein the surface of the ferromagnetic part is substantially vertical.

8. A method comprising:
magnetizing a ferromagnetic part to be inspected, wherein a defect in or near a surface of the ferromagnetic part causes an external magnetic field;
positioning a magnetic field sensing element near the ferromagnetic part for sensing the external magnetic field, wherein the magnetic field sensing element includes a magnetic sheet material including a pre-determined tracer pattern;
identifying the defect in or near the surface of the ferromagnetic part by interpreting data collected by the magnetic field sensing element in response to the magnetic field sensing element being placed near the ferromagnetic part, wherein the data includes a physical change in the pre-determined tracer pattern caused by the external magnetic field; and
creating a data storage file regarding any identified defect in or near the surface of the ferromagnetic part.

* * * * *